(12) United States Patent
Chayet et al.

(10) Patent No.: US 7,125,405 B1
(45) Date of Patent: Oct. 24, 2006

(54) METHOD FOR CALCULATING REFRACTIVE CORRECTION AMOUNT IN CORNEAL REFRACTIVE SURGERY

(75) Inventors: Arturo S. Chayet, Tijuana (MX); Yoshitaka Suzuki, Okazaki (JP)

(73) Assignee: Nidek Co., Ltd. (JP)

( * ) Notice: Subject to any disclaimer, the term of this patent is extended or adjusted under 35 U.S.C. 154(b) by 0 days.

(21) Appl. No.: 09/609,144

(22) Filed: Jun. 30, 2000

Related U.S. Application Data

(63) Continuation of application No. 09/121,917, filed on Jul. 24, 1998.

(51) Int. Cl.
*A61F 9/008* (2006.01)

(52) U.S. Cl. .............................. 606/10; 606/5; 606/13

(58) Field of Classification Search ................ 128/898; 606/5, 10–12, 166
See application file for complete search history.

(56) References Cited

U.S. PATENT DOCUMENTS

| | | | |
|---|---|---|---|
| 5,637,109 A | 6/1997 | Sumiya | |
| 5,713,892 A | 2/1998 | Shimmick | |
| 5,800,424 A | 9/1998 | Sumiya | |

FOREIGN PATENT DOCUMENTS

| | | |
|---|---|---|
| DE | 19522915 | 1/1996 |
| EP | 628298 | 12/1999 |
| JP | 9-122167 | 5/1997 |
| WO | 95/27452 | * 10/1995 |

OTHER PUBLICATIONS

Chayet et al "Laser in situ Keratomileusis for Simple Myopic, Mixed, and Simple Hyperopic Astigmatism"; J. Refract. Surg.; V14, No. 2 (Suppl), Apr. 1998, pp. S175-S176.*

Chayet, S. Arturo, et al., "Laser in situ Keratomileusis for Simple Myopic, Mixed, and Simple Hyperopic Astigmatism," Journal of Refractive Surgery, vol. 14, No. 2 (suppl.), pp. S175-S176, Apr. 1998.

Lucio Buratto et al., Indications, techniques, results, and complications of laser in *situ* keratomileusis, Current Opinion in Ophthalmology, vol. 8, No. 4, pp. 59-66, Aug. 1997.

\* cited by examiner

*Primary Examiner*—David M. Shay
(74) *Attorney, Agent, or Firm*—Finnegan, Henderson, Farabow, Garrett & Dunner, LLP

(57) ABSTRACT

An apparatus for operation on a cornea by ablating with a laser beam for correcting ametropia; the apparatus comprising an input device utilized for inputting each data necessary for correction, a first correcting device for irradiating a laser beam for correcting myopic astigmatism, a second correcting device for irradiating a laser beam for correcting hyperopic astigmatism, a calculating device for calculating each correction-data based on the each inputted data in case of combining the first and second correcting means, and a control device for ablating the cornea by controlling the first and second correcting means based on results calculated by the calculating device.

4 Claims, 2 Drawing Sheets

METHOD FOR CALCULATING REFRACTIVE CORRECTION AMOUNT IN CORNEAL REFRACTIVE SURGERY

The present invention is a continuation of application Ser. No. 09/121,917, filed Jul. 24, 1998, pending.

BACKGROUND OF THE INVENTION

1. Field of the Invention

The present invention relates to an apparatus for operation on a cornea, and more particularly to the apparatus which corrects ametropia by ablating a corneal surface with a laser beam, being suitable for correcting simple myopic astigmatism and mixed astigmatism.

2. Description of Related Art

In conventional art, there is known an apparatus for operation on a cornea, which corrects ametropia of an examined eye by ablating a corneal surface with an excimer laser. Several methods have been proposed for laser irradiation for such a kind of the apparatus, to include a one shot irradiation method which covers an irradiation area of a cornea with only one shot, a scanning slit method which puts side by side with superposing a slit (rectangular) shaped laser beam in a width direction, and a scanning spot method which converges a laser beam to a diameter of 1 to 2 mm, then scans with high velocity by wagging the laser beam with a mirror having two axes of X and Y. The apparatus acting on above mentioned method enables one to perform such operations as to correct myopia and compound myopic astigmatism, further enabling one to correct hyperopia.

A typical method of correcting myopic astigmatism is to flatten the cornea in a strong principal meridian direction. One such method is to ablate the whole cornea in a strong principal meridian direction by enlarging an optical zone, and the other method is to ablate only a central part in a strong principal meridian direction selectively.

However, since a corneal surface is curved, a central part of cornea differs from that of a periphery of cornea in an energy density of a laser irradiation. Accordingly, in case of the method of correcting myopic astigmatism by ablating the whole in a strong principal meridian direction, an ablation of the periphery tends to be slight as a whole, thus resulting in such a problem that a spherical component is shifted to a hyperopic direction.

On the contrary, in the case of the method of correcting myopic astigmatism by ablating only a central part in a strong principal meridian direction selectively, since a small area in a strong principal meridian direction can be ablated, a spherical component is shifted little. However, because of a small optical zone, there is such a problem that a patient's eye is influenced by an optical disorder such a as glare or a halo.

In addition, in the case of correction for mixed astigmatism showing such symptoms as to be myopia on a strong principal meridian and to be hyperopia on a weak principal meridian, a method combines an ablation in a strong principal meridian direction with an ablation for correcting hyperopia. By combining simply, there are such problems that an ablation amount becomes much and a satisfactory result is not obtained.

SUMMARY OF THE INVENTION

The present invention has been made in view of the above circumstances and has an object to overcome the above problems and to provide an apparatus for use in operating on a cornea, which can correct astigmatism, such as simple myopic astigmatism and mixed astigmatism, accurately and easily by ablating the whole of an optical zone.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an apparatus for operation on a cornea by ablating with a laser beam for correcting ametropia, the apparatus of this invention comprises input means utilized for inputting each data necessary for correction, first correcting means for irradiating a laser beam for correcting myopic astigmatism, second correcting means for irradiating a laser beam for correcting hyperopic astigmatism, calculating means for calculating each correction-data based on the inputted data in the case of combining the first and second correcting means, and control means for ablating the cornea by controlling the first and second correcting means based on results calculated by the calculating means.

Another aspect of the present invention, an apparatus for operation on a cornea by ablating with a laser beam for correcting ametropia, the apparatus comprises first correcting means for irradiating a laser beam for correcting myopic astigmatism, second correcting means for irradiating a laser beam for correcting hyperopic astigmatism, data input means utilized for inputting each data, such as an amount of astigmatism correction and a direction of a cylindrical axis, which is to be corrected by the first and second means in order to correct simple myopic or mixed astigmatism, and control means for ablating a cornea by controlling the laser irradiation performed by the first and second correcting means based on the inputted data.

Further, another aspect of the present invention, an apparatus for operation on a cornea, comprises irradiation optical system for irradiating a laser beam for surgery onto a patient's cornea, moving means for moving the laser beam to a direction intersecting with an optical axis of the irradiation optical system, rotation means for causing the laser beam to rotate around the optical axis of the irradiation optical system, a circular aperture for restricting a corneal ablation area to be ablated by the laser beam, disposed at the irradiation optical system, a slit aperture for limiting the ablation area limited by the circular aperture to be a slit-shape, the slit aperture being variable, data input means utilized for inputting each data necessary for desiring a corneal shape after the ablation, first irradiating means for irradiating a laser beam by causing a width of the slit aperture to vary toward a strong principal meridian direction for correcting astigmatism, under the condition that the laser beam is rotated by the rotation means every time when the laser beam is scanned by the moving means, second irradiating means for irradiating a laser beam by shifting a position of the laser beam moved by the moving means under the condition that the laser beam is rotated by the rotation means so that a moving direction of the laser beam by the moving means may vary toward a weak principal meridian direction for correcting astigmatism within an area limited by the circular aperture, and control means for calculating each amount of ablation in both strong and weak principal meridian directions based on the data inputted by the data input means, and controlling combination of the first and second irradiating means based on the amount of ablation.

According to the present invention, simple myopic astigmatism and mixed astigmatism can be corrected accurately and easily by utilizing an optical zone at which a patient's eye is not influenced. In addition, in the case of combining an ablation in a strong principal meridian direction with an ablation in a weak principal meridian direction, the apparatus is configured so as to calculate data utilized for converting an astigmatism sign and a rotation of a cylindrical axis, therefore, accurate laser irradiation can be performed with avoiding a possible serious involvement induced by disorder of a cylindrical axis.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

A detailed description of one preferred embodiment of an apparatus for operation on a cornea embodying the present invention will now be given referring to the accompanying drawings. Firstly, a method of correcting myopic astigmatism and mixed astigmatism according to the present invention will be described below.

Figure 1:
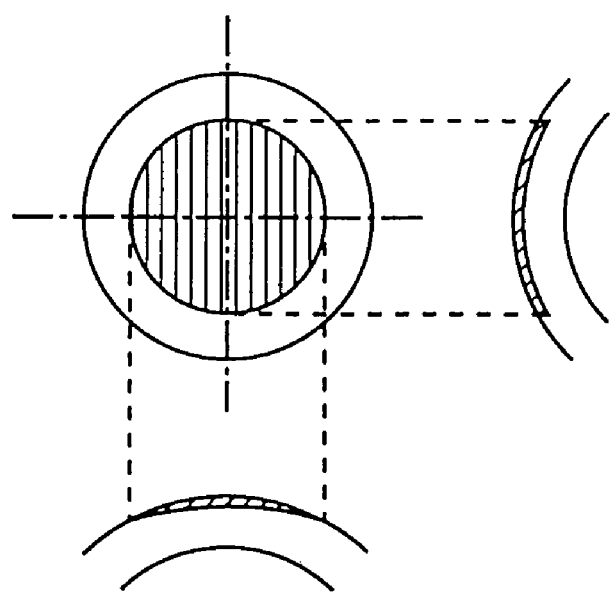
FIG. 1 is a schematic view showing a corneal part to be ablated in order to correct myopic astigmatism.

As shown in FIG. 1, correction for simple myopic astigmatism is performed by ablating a cornea to be a shape similar to a convex cylindrical lens such that a central part is deeply ablated and a periphery is slightly ablated in a certain direction (in a strong principal meridian direction) of a whole optical zone. However, as described above, a central part of a cornea differs from that of a periphery of cornea in an energy density of a laser irradiation. Because of the difference, a spherical component is shifted, thereby correction for simple myopic astigmatism can not performed. Referring to clinical results made by the present inventors, a ratio of a hyperopic shift of spherical component to a correction amount of cylindrical component is approximately 30%–50%, and an average is approximately 33%.

A residual spherical component after ablation of a cylindrical component can be corrected by combining myopic astigmatism correction with an ablation of hyperopic correction which is performed by ablating a central part to be slightly ablated and ablating a periphery to be deeply ablated. However, an amount of ablation of corneal tissues becomes large. The same is true in the case of mixed astigmatism.

Figure 2:
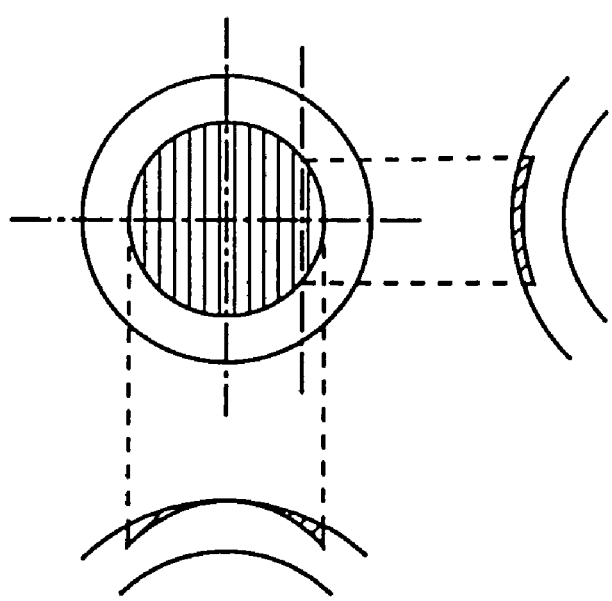
FIG. 2 is a schematic view showing a corneal part to be ablated in order to correct hyperopic astigmatism.

In contrast to above mentioned correction for myopic astigmatism (FIG. 1), FIG. 2 shows the case of correction for hyperopic astigmatism which ablates a central part slightly and a periphery deeply in a weak principal meridian direction, an amount of laser beam necessary for irradiating a central part is allowed to be little. Therefore, only a weak principal meridian direction can be steep without affecting a strong principal meridian direction basically.

Accordingly, in the case of correction for simple myopic astigmatism and mixed astigmatism, considering a ratio of a shift of a spherical component in case of correcting myopic astigmatism in a strong principal meridian direction, a laser irradiation for correcting hyperopic astigmatism which does not affect a strong principal meridian direction is combined with a laser irradiation for correcting myopic astigmatism. Thereby, correction for simple myopic and mixed astigmatism may be possible in which an amount of ablation of corneal tissues decreases as a whole.

Next, calculation for each amount of ablation according to the combination will be described below. It is assumed that preoperative refractive powers such as S (a spherical power), C (a cylindrical power) and A (a cylindrical axis) are corrected so as to be emmetropia. Further, preoperative cylindrical power C is assumed as a minus power.

Firstly, it is assumed that an amount of astigmatism correction $C_{Myo}$ of a cylindrical power C is ablated by correction for myopic astigmatism in a strong principal meridian direction. By the ablation, if X% of $C_{Myo}$ is assumed as being shifted to a spherical component (a hyperopic shift), then each residual power is (S+$C_{Myo}$·X, C+$C_{Myo}$, A).

The residual spherical power (S+$C_{Myo}$) is made to be able to be corrected by way of an ablation for correcting hyperopic astigmatism. That is, a residual spherical power may be made to be approximately zero when converting a residual cylindrical power (C+$C_{Myo}$) into a plus power. At this time, a cylindrical axis is changed 90° (in case of A=0° to 90°, it is defined as A+90°, in case of A=91° to 180°, it is defined as A−90°).

With definitions as above, an amount of astigmatism correction $C_{Myo}$ which is to be ablated by correction for myopic astigmatism is given by the following expression (1):

$$C_{Myo} = \frac{|S+C|}{1+X} \quad (1)$$

If an amount of astigmatism correction which is to be ablated by correction for hyperopic astigmatism is defined as $C_{Hyp}$, then following expression (2) is given:

$$C_{Hyp} = |C| - C_{Myo} \quad (2)$$

For example, in case of simple myopic astigmatism of which a preoperative refractive power is given by (S:0 (Plano), C:−3.00, A:0), if a ratio X of a spherical component shift caused by correction for myopic astigmatism in a strong principal meridian direction is defined as 0.33 (33%), then an amount ablated by correction for myopic astigmatism is given by $C_{myo}$=2.25(D). It corresponds to 75% of a preoperative amount of astigmatism. By the correction, a 0.75(D) of a spherical component shifts to a hyperopic direction, thus leaving a refractive power (S:+0.75, C:−0.75, A:0). Where, if a sign of the cylindrical power is converted to a plus sign, a refractive power (S:0, C:+0.75, A:90) is obtained. This indicates an amount $C_{Hyp}$=0.75(D) ablated by correction for hyperopic astigmatism, which corresponds to 25% of a preoperative amount of astigmatism.

In addition, in the case of mixed astigmatism of which a preoperative refractive power is given by (S:+2.00, C:−4.00, A:0), if a ratio X of a spherical component shift caused by correction for myopic astigmatism is defined as 0.33 (33%), then an amount of correction is given by $C_{myo}$=1.5(D). It indicates that 37% of a preoperative amount of astigmatism is to be ablated by using an ablation in a strong principal meridian direction. Accordingly, after 33% of a spherical component shift, a refractive power (S:+2.5, C:−2.5, A:0) is left. Where, if a sign of a cylindrical power is converted to a plus sign, then a refractive power (S:0, C:+2.5, A:90) is obtained, being an ideal value for an ablation in a weak principal meridian direction. At this time, an amount of correction is given by $C_{Hyp}$=2.5(D), which corresponds to 63% of a preoperative amount of astigmatism.

Table I shows each amount of astigmatism correction relative to each refractive power for correcting simple myopic astigmatism or mixed astigmatism, upon combining an ablation for correcting myopic astigmatism with an ablation for correcting hyperopic astigmatism as described above (assuming that 33% of a cylindrical component shifts to a spherical component caused by an ablation for correcting myopic astigmatism in a strong principal meridian direction).

TABLE 1

| Refraction | | | |
|---|---|---|---|
| S | C | Steep Meridian (D) | Flat Meridian (D) |
| −1.00 | −5.00 | 4.5 | 0.5 |
| −1.00 | −6.00 | 5.25 | 0.75 |
| −1.00 | −7.00 | 6.00 | 1.0 |
| 0.00 | −2.00 | 1.5 | 0.5 |
| 0.00 | −3.00 | 2.25 | 0.75 |
| 0.00 | −4.00 | 3.00 | 1.0 |
| 0.00 | −5.00 | 3.75 | 1.25 |
| 0.00 | −6.00 | 4.5 | 1.5 |
| 0.00 | −7.00 | 5.25 | 1.75 |
| +1.00 | −2.00 | 0.75 | 1.25 |
| +1.00 | −3.00 | 1.5 | 1.5 |
| +1.00 | −4.00 | 2.25 | 1.75 |
| +1.00 | −5.00 | 3.00 | 2.00 |
| +1.00 | −6.00 | 3.75 | 2.25 |
| +1.00 | −7.00 | 4.5 | 2.5 |
| +2.00 | −3.00 | 0.75 | 2.25 |
| +2.00 | −4.00 | 1.5 | 2.5 |
| +2.00 | −5.00 | 2.25 | 2.75 |
| +2.00 | −6.00 | 3.00 | 3.00 |
| +2.00 | −7.00 | 3.75 | 3.25 |
| +3.00 | −4.00 | 0.75 | 3.25 |
| +3.00 | −5.00 | 1.5 | 3.5 |
| +3.00 | −6.00 | 2.25 | 3.75 |
| +3.00 | −7.00 | 3.00 | 4.00 |
| +4.00 | −5.00 | 0.75 | 4.25 |
| +4.00 | −6.00 | 1.50 | 4.50 |
| +4.00 | −7.00 | 2.25 | 4.75 |

Figure 3:
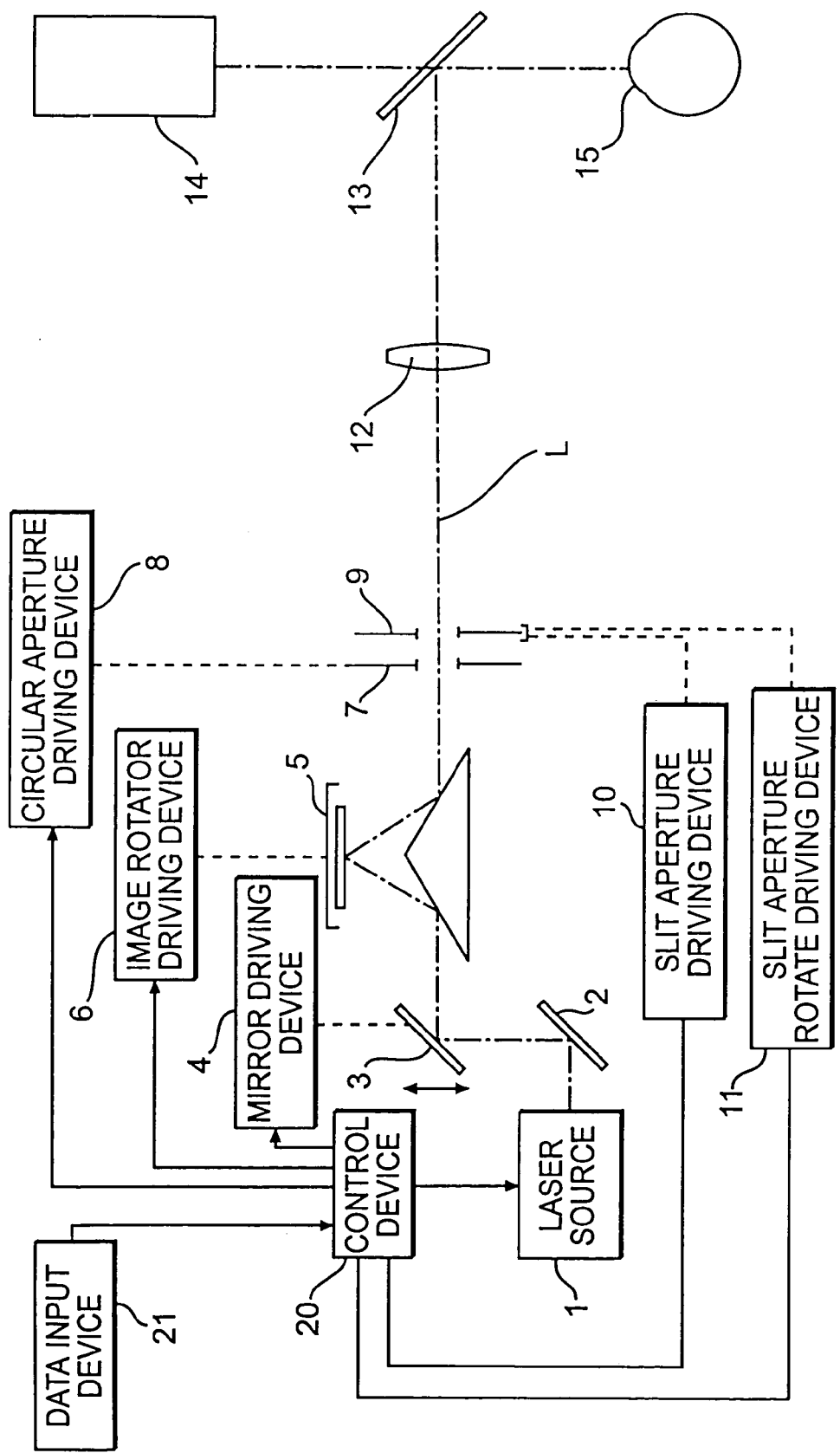
FIG. 3 is a view showing a schematic arrangement of an optical system and a schematic construction of a control system of an apparatus of a preferred embodiment of the present invention.

FIG. 3 shows a block diagram of a preferred embodiment an apparatus for operation on a cornea configured so as to perform above mentioned correction, showing a schematic arrangement of an optical system and a schematic construction of a control system.

Reference numeral 1 is a laser source for which an excimer laser having wavelength of 193 nm is used in the preferred embodiment. Laser beam from the laser source 1 is a pulse, of which a typical shape is as follows. That is, intensity distribution of the beam is uniform in a horizontal direction, and a vertical direction is Gaussian distribution. In addition, a sectional shape of a plane intersecting an optical axis at right angles is an elongated slit (rectangular) shape. The shape can be changed to be a desired shape in case of need by utilizing a beam reforming means such as an expander lens and the like.

Laser beam from the laser source 1 is deflected upward by a plane mirror 2, further being deflected horizontally by a plane mirror 3. The plane mirror 3 is movable parallel to the arrow by a mirror driving device 4, which makes a laser beam be in parallel motion toward Gaussian distribution direction so that a cornea is ablated uniformly.

Reference numeral 5 is an image rotator which is driven so as to rotate by an image rotator driving device 6 with the center at the optical axis L, thereby causing a laser beam to rotate about the optical axis L. Reference numeral 7 is a variable circular aperture which restricts an ablation area, an aperture width being varied by a circular aperture driving device 8. Reference numeral 9 is a slit aperture which limits an ablation area to be a shape of a slit, an aperture width being varied by a slit aperture driving device 10. In addition, the slit aperture 9 is rotated around the optical axis L by the slit aperture rotate driving device 11, thereby a direction of a slit aperture is changed. The slit aperture 9 is utilized for correcting myopic astigmatism and the like.

Reference numeral 12 is a projecting lens which projects the circular aperture 7 and/or the slit aperture 9 onto a cornea 15 of the patient. An image of the area restricted by the circular aperture 7 and/or the slit aperture 9 is formed on the cornea 15.

Reference numeral 13 is a dichloic mirror having such characteristic that reflects an excimer laser having wavelength of 193 nm and transmits a visible ray. Laser beam passed through the projecting lens 12 is reflected by the dichloic mirror 13, then being delivered to the cornea 15. Reference numeral 14 is an observation optical system which is provided with a binocular microscope for surgery (goods on the market can be utilized), which is arranged above the dichloic mirror 13. In addition, prior to a surgery, the patient's eye is made to be at a predetermined position in advance, thereby causing the eye to be made to look at a fixation target (not shown) in order to keep the positional condition of the eye.

Reference numeral 20 is a control device which controls the laser source 1, respective driving devices 4, 6, 8, 10 and 11. Reference numeral 21 is a data input device which is utilized for inputting each data necessary for correction for the patient's eye.

Next, each method of a laser irradiation for correcting myopia, hyperopia, hyperopic astigmatism, myopic astigmatism and mixed astigmatism will be described by utilizing the apparatus having above mentioned architecture.

[Correction for Myopia]

In the case of correction for myopia, a laser beam is limited by the circular aperture 7, and the plane mirror 3 is moved in order, causing the laser beam to be moved to Gaussian distribution direction. Every time when the laser beam finishes moving over one plane (per one scanning), a rotation of the image rotator 5 is made to change a moving direction of the laser beam (three directions at equal angular intervals of say 120°), thereby the area limited by the circular aperture 7 is ablated approximately uniformly. By performing the ablation every time when a size of an opening of the circular aperture 7 is changed, thereby such myopia correction is performed that a central part of cornea is deeply ablated and a periphery of cornea is slightly ablated (details are mentioned in U.S. Pat. No. 5,637,109).

[Correction for Hyperopia]

In the case of correction for hyperopia, a size of an opening of the circular aperture 7 is fixed, thereby the ablation area is limited. Then, the plane mirror 3 is shifted relative to the optical axis L, causing the laser beam to be deviated, and the image rotator 5 is made to rotate, causing the ablation to be repeated, thereby the cornea is ablated to be circular (ringed). The plane mirror 3 is moved in order, thereby a shifted amount of the laser beam from the optical axis L increases. In accordance with the increase, a number of irradiation pulses (irradiation time) is made to be increased. Thereby such correction for hyperopia can be performed that a central part of cornea is slightly ablated and a periphery of cornea is deeply ablated. To control a diopter is performed by way of varying a whole number of irradiation pulses without varying a ratio of a number of irradiation pulses at each position of a laser beam which is shifted from the optical axis L in accordance with a movement of the plane mirror 3 (details are mentioned in Japanese Patent Laid-open Hei.9-122167 corresponding to DE19522915A1).

[Correction for Hyperopic Astigmatism]

In the case of correction for hyperopic astigmatism, a size of an opening of the circular aperture 7 is fixed, thereby the ablation area is limited, and the plane mirror 3 is made to move gradually, thus causing the laser beam to move to Gaussian distribution direction. At this time, a moving direction of the laser beam on the cornea is adjusted by a rotation of the image rotator 5 so as to be a weak principal meridian direction. Then, the laser beam is made to be shifted gradually, and a number of irradiation pulses at each position is made to increase with an appropriate ratio as the laser beam comes to be close to a periphery. Accordingly, in a weak principal meridian direction, such ablation is performed that a central part is slightly ablated and a periphery is deeply ablated (see Japanese Patent Laid-open Hei.9-122167). A residual spherical component can be treated by combining it with above mentioned correction for hyperopia.

[Correction for Myopic Astigmatism and Mixed Astigmatism]

The correction is performed by combining a laser irradiation method for correcting myopic astigmatism in a strong principal meridian direction with above mentioned laser irradiation method for correcting hyperopic astigmatism. The irradiation method for correcting myopic astigmatism in a strong principal meridian direction is as follows.

A size of an opening of the circular aperture 7 is fixed in accordance with the optical zone, then an opening width of the slit aperture 9 is made to be varied. Prior to this operation, a direction of the slit aperture 9 is adjusted by the slit aperture rotate driving device 11 so that the opening width of the slit aperture 9 may vary toward a strong principal meridian direction. The laser irradiation is performed the same as above mentioned correction for myopia, that is, firstly, the plane mirror 3 is made to move in order, causing the laser beam to moved to Gaussian distribution direction. Then, every time when the laser beam is scanned, a moving direction of the laser beam is changed by a rotation of the image rotator 5, thereby causing the area limited by the slit aperture 9 to be ablated uniformly. With varying the opening width of the slit aperture 9 in order, the ablation is repeated many times, thus causing a strong principal meridian direction to be flattened, thereby correction for astigmatism is performed.

With this laser irradiation method, an ablation is performed in accordance with an amount of astigmatism correction $C_{Myo}$. Concerning a residual amount of correction, an ablation is performed in accordance with an amount of astigmatism correction $C_{Hyp}$ with a laser irradiation method for correcting hyperopic astigmatism.

Next, an actual operation of the apparatus upon operating on the cornea in order to correct ametropia will be described below. Firstly, in accordance with a kind of ametropia, a correcting mode is selected by using the data input device 21. Upon correcting normal ametropia such as myopia, hyperopia and hyperopic astigmatism, a NORMAL MODE is selected. Upon correcting simple myopic astigmatism and mixed astigmatism, a MIX MODE is selected, which combines a laser irradiation method for correcting myopic astigmatism with a laser irradiation method for correcting hyperopic astigmatism. The assumptions for the MIX MODE are as follows.

(1) A correcting refractive power is such that a cylindrical component is considered as a minus power.

(2) A spherical component of +1.0D to −1.0D, never to exceed 30% of the cylindrical component, is classified into simple myopic astigmatism.

(3) A cylindrical component is no more than 7D: where a spherical equivalent of +1.5D to −2.5D is classified into mixed astigmatism.

After selecting the MIX MODE, if data of each correcting refractive power (preoperative and postoperative correcting refractive powers) is inputted, then the control device 20 calculates amounts of astigmatism correction both of strong and weak principal meridian directions by way of above mentioned method. In case of correction for astigmatism in a weak principal meridian direction, the apparatus is configured so as to convert a sign of a cylindrical component relative to an inputted cylindrical axis and to change the cylindrical axis 90°, thus obtaining data. In addition, for each data necessary for operating on a cornea, such as a preoperative corneal shape, an optical zone and the like, the control device 20 obtains each data for controlling a laser irradiation based on the data.

After aligning the optical axis of a laser irradiation with the patient's eye, if a trigger signal is inputted with a switch, not shown, then the control device 20 controls the laser source 1 and each driving device, thereby performing above mentioned laser irradiation for correcting both hyperopic astigmatism and myopic astigmatism. Accordingly, the patient's eye is ablated so as to be a desired shape, thus causing ametropia to be corrected.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A method for calculating an ablation amount for refractive correction in corneal refractive surgery to be achieved by ablating an optical zone of a cornea of an eye to be operated with a laser beam, the method comprising:
   a first step of inputting data necessary for correcting simple myopic astigmatism or mixed astigmatism; and
   a second step of dividing a total ablation amount into a first ablation amount for myopic astigmatism correction and a second ablation amount for hyperopic astigmatism correction based on the inputted data in accordance with a given standard, in the myopic astigmatism correction, a portion of the cornea closer to a weak principal meridian being ablated more and a portion of the cornea farther from the weak principal meridian being ablated less, and in the hyperopic astigmatism correction, a portion of the cornea closer to a strong principal meridian being ablated less and a portion of the cornea farther from the strong principal meridian being ablated more.

2. The method according to claim 1, wherein the second step divides the total ablation amount into the first ablation amount and the second ablation amount in accordance with a ratio of change in a spherical component to be effectuated by the first ablation amount.

3. The method according to claim 1, wherein the second step calculates the first ablation amount using the following expression:

$$C_{Myo}|S+C|/(1+x)$$

and calculates the second ablation amount using the following expression:

$$C_{Hyp}=|C|-C_{Myo}$$

in a case wherein x is a ratio of change in a spherical component to be effectuated by the first ablation amount, and the data necessary for correcting the simple myopic astigmatism or the mixed astigmatism with spherical power S and astigmatic or cylindrical power C is inputted.

4. The method according to claim 1, wherein the second step divides the total ablation amount into the first ablation amount and the second ablation amount in accordance with a table having interrelated lists of the first ablation amount and of the second ablation amount.

* * * * *